United States Patent [19]
Schmidt

[11] Patent Number: 4,546,178
[45] Date of Patent: Oct. 8, 1985

[54] PROCESS FOR PREPARING VIRTUALLY ISOMER-FREE 4-AMINO-3-ETHYLTHIO-6-TERT.-BUTYL-1,2,4,-TRIAZIN-5-ONE

[75] Inventor: Thomas Schmidt, Haan, Fed. Rep. of Germany

[73] Assignee: Bayer Aktiengesellschaft, Leverkusen, Fed. Rep. of Germany

[21] Appl. No.: 666,576

[22] Filed: Oct. 30, 1984

[30] Foreign Application Priority Data

Nov. 4, 1983 [DE] Fed. Rep. of Germany ....... 3339858

[51] Int. Cl.⁴ .......................................... C07D 253/06
[52] U.S. Cl. .................................................... 544/182
[58] Field of Search .......................................... 544/182

[56] References Cited

U.S. PATENT DOCUMENTS

| | | | |
|---|---|---|---|
| 4,309,538 | 1/1982 | Schmidt et al. | 544/182 |
| 4,315,094 | 2/1982 | Bonse et al. | 544/182 |
| 4,328,340 | 5/1982 | Bonse et al. | 544/182 |
| 4,408,044 | 10/1983 | Schmidt et al. | 544/182 |

Primary Examiner—John M. Ford
Attorney, Agent, or Firm—Sprung, Horn, Kramer & Woods

[57] ABSTRACT

In the preparation of amino-3-ethylthio-6-tert.-butyl-1,2,4-triazin-5-one (I) by reacting 4-amino-3-mercapto-6-tert.-butyl-1,2,4-triazin-5-one (II) with an ethylating agent in aqueous alkali solution, the improvement which comprises contacting the reaction mixture with at least 50 g of petroleum ether per mole of starting compound (II) at a temperature of about 40°–60° C. thereby forming two liquid phases, and cooling the mixture down to about room temperature, whereby substantially pure isomer-free end product of the formula (I) crystallizes out.

5 Claims, No Drawings

PROCESS FOR PREPARING VIRTUALLY ISOMER-FREE 4-AMINO-3-ETHYLTHIO-6-TERT.-BUTYL-1,2,4,-TRIAZIN-5-ONE

The invention relates to a process—which can also be used in industry—for preparing virtually isomer-free 4-amino-3-ethylthio-6-tert.-butyl-1,2,4-triazin-5-one (I) which is a well known herbicidal active substance which can be isolated from the reaction mixture by the new method so highly selectively as to be no more than insignificantly contaminated by the unwanted, non-herbicidally active N-ethylated 2-ethyl-3-thioxo derivative (Ia).

It has already been disclosed that 4-amino-3-ethylthio-6-tert.-butyl-1,2,4-triazin-5-one (I) is obtained when 4-amino-3-mercapto-6-tert.-butyl-1,2,4-triazin-5-one (II) is reacted in alkaline solution with an ethylating agent, such as ethyl iodide or ethyl bromide (compare for example U.S. Pat. No. 3,671,523).

However, this process has the disadvantage that, in addition to the desired S-ethylated end product of the formula (I), it produces about 15% of unwanted N-ethylated by-product of the formula (Ia):

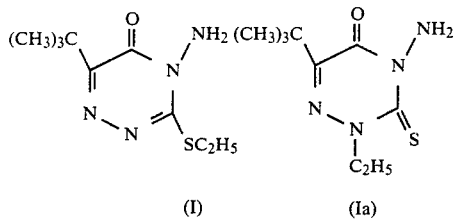

It is a further disadvantage that this mixture is difficult to separate into its components using conventional industrial methods. One-step recrystallization results in loss of material, is technically complicated, and merely has the effect of reducing the proportion of N-ethylated by-product of the formula (Ia) to about 6%.

It has now been found that the known 4-amino-3-ethylthio-6-tert.-butyl-1,2,4-triazin-5-one of the formula (I)

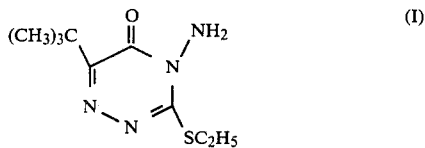

is iobtained in high yield and purity, even on an industrial scale, by reacting 4-amino-3-mercapto-6-tert.-butyl-1,2,4-triazin-5-one which can exist in two tautomeric forms having the formulas (II)

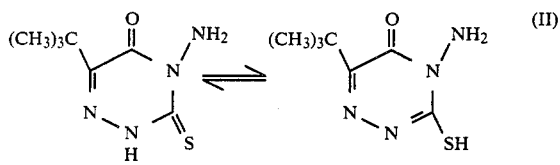

with an ethylating agent in aqueous alkali solution when at least 50 g of petroleum ether—relative to 1 mole of starting compound (II)—are added at a temperature of 40°-60° C. to the thoroughly stirred reaction mixture, the reaction mixture, now consisting of two liquid phases, is then cooled down to room temperature, and the pure end product of the formula (I) which crystallizes out in the course of the cooling is isolated in conventional manner.

It must be regarded as very surprising that the 4-amino-3-ethylthio-6-tert.-butyl-1,2,4-triazin-5-one of the formula (I) can be obtained by this process in high yield and purity since—as in-house experiments have shown—recrystallizing the isolated and dried crude active substance (comprising products (I) and (Ia) in an approximate ratio of 85:15) from petroleum ether only has an unsatisfactory purification effect.

Surprisingly, petroleum ether—as further experiments have shown—cannot be replaced by other similar solvents such as, for example, cyclohexane without the purification effects obtained being much worse.

It is also surprising that in the case of the S-methyl and N-methyl compounds corresponding to the pair of isomers (I)/(Ia) the same method is not successful in separating the isomers. This is true, for example, for the technical-grade active substance 4-amino-3-methylthio-6-tert.-butyl-1,2,4-triazin-5-one which, from the industrial synthesis, contains about 6% of isomeric 4-amino-2-methyl-3-thioxo-6-tert.-butyl-1,2,4-triazin-5-one.

The process according to the invention has the advantage of producing a high purification effect while losing very little product. The desired product—even if prepared on an industrial scale—is obtained in about 97% purity and a simultaneously high space-time yield (throughput). A further advantage is that the process is so simple to carry out as to avoid any need for a separate, costly recrystallization.

The 4-amino-3-mercapto-6-tert.-butyl-1,2,4-triazin-5-one of the formula (II) which is to be used as a starting material is known (compare for example U.S. Pat. No. 3,671,523).

The ethylating agent is preferably an ethyl halide, such as ethyl chloride, ethyl bromide or ethyl iodide, diethyl sulphate, triethyl phosphate, triethyl phosphite, ethyl methanesulphonate or ethyl p-toluenesulphonate.

The reaction with the ethylating agent is carried out in the presence of a base. This base is preferably any conventional strong inorganic base, such as sodium hydroxide, potassium hydroxide or calcium hydroxide, each in the form of an aqueous solution.

In carrying out the ethylation, 0.1 to 5, preferably 0.3 to 2, moles of ethylating agent and 1 to 10 moles, preferably 1 to 5 moles, of aqueous base are used per mole of compound of the formula (II).

Before, during or after the ethylation, petroleum ether is added with vigorous stirring to the reaction mixture at a temperature of 40°-60° C., preferably 40°-50° C. For the purposes of the present invention, the petroleum ether can be any of the various fractions of industrial hydrocarbon distillation, such as, in particular, one of the fractions boiling between 100° and 140° C. In general, 50 to 400 g, preferably 100-250 g, of petroleum ether are used per mole of starting compound of the formula (II).

The process according to the invention can be carried out particularly advantageously as follows:

1 mole of 4-amino-3-mercapto-6-tert.-butyl-1,2,4-triazin-5-one of the formula (II) is dissolved in the specified amount of aqueous base, and 0.3 to 2 moles of ethylating agent are added. The reaction takes two to eight hours at a temperature of 40°-60° C. The specified amount of petroleum ether is added to the reaction mixture, which is then cooled down to about 20° C. during which the desired end product of the formula (I) crystallizes out. The solid material is filtered off, is washed until neutral, and is dried in vacuo.

It should be emphasized that the reaction need not be carried out until all of the starting material of the formula (II) has reacted, but it can also be discontinued before such a time. Unreacted starting material of the formula (II) remains in solution and, once the petroleum ether phase has been separated off, can be re-used with the mother liquor in a subsequent batch.

The compound of the formula (I) is known to have very high herbicidal activity (compare U.S. Pat. No. 3,671,523).

The process according to the invention is illustrated in more detail, and compared with the state of the art, in the following example of a preparation:

PREPARATION EXAMPLE

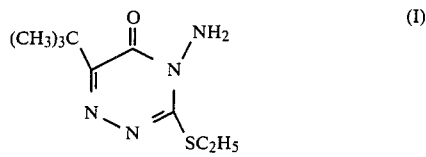

(a) in accordance with the invention (on an industrial scale):

147.15 kg (0.736 kMol) of 4-amino-3-mercapto-6-tert.-butyl-1,2,4-triazin-5-one (II), 600 kg of water, 75 kg of 45% strength sodium hydroxide solution and 90 kg (0.826 kMol) of ethyl bromide are stirred in a 1,250 liter stirred vessel at an internal temperature of 40°-50° C. for 5 hours. 167 kg of petroleum ether (the fraction of the industrial hydrocarbon distillation boiling between 100° and 140° C.) are then added to the vessel at said temperature, and the temperature is reduced to about 20° C. The solid material which has crystallied out in the course of the cooling is filtered off, is washed three times with 150 kg of 1% strength sodium hydroxide solution each time and three times with 150 kg of water each time, and is dried in vacuo.

This gives 113.2 kg (78% of theory relative to reacted starting material of the formula (II)) of 4-amino-3-ethylthio-6-tert.-butyl-1,2,4-triazin-5-one having a melting point of 92°-94° C. and a composition (determined by gas chromatography) of 96.9% 4-amino-3-ethylthio-6-tert.-butyl-1,2,4-triazin-5-one (I) and 2.7% 4-amino-2-ethyl-3-thioxo-6-tert.-butyl-1,2,4-triazin-5-one (Ia).

By acidifying the combined mother and wash liquors in the customary manner it is possible to recover 20 kg of 4-amino-3-mercapto-6-tert.-butyl-1,2,4-triazin-5-one (II).

The petroleum ether phase contains 19.1 kg of 4-amino-2-ethyl-3-thioxo-6-tert.-butyl-1,2,4-triazin-5-one (Ia) (13.2% of theory relative to reacted starting material of the formula (II)) and 0.83 kg of 4-amino-3-ethylthio-6-tert.-butyl-1,2,4-triazin-5-one (I) (0.57% of theory relative to reacted starting material of the formula (II)).

(b) in accordance with the state of the art (comparative experiment):

128 g (1.17 moles) of ethyl bromide are added at 45° C. to a solution prepared in a 2-liter three-necked flask from 200 g (1 mole) of 4-amino-3-mercapto-6-tert.-butyl-1,2,4-triazin-5-one (II) in 1,800 ml of water and 60 g of 25% strength sodium hydroxide solution. After addition of a further 114 g of 25% strength sodium hydroxide solution the reaction mixture is stirred at 45° C. for 8 hours, is cooled down to 20° C., and is filtered. The solid material remaining on the filter is washed twice with 180 ml of 1% strength sodium hydroxide solution each time and three times with 180 ml of water each time and is dried at 50° C. in vacuo. This gives 182 g (75.7% of theory relative to reacted starting material of the formula (II)) of 4-amino-3-ethylthio-6-tert.-butyl-1,2,4-triazin-5-one having a composition (determined by gas chromatography) of 85.54% 4-amino-3-ethylthio-6-tert.-butyl-1,2,4-triazin-5-one (I) and 14.46% 4-amino-2-ethyl-3-thioxo-6-tert.-butyl-1,2,4-triazin-5-one (Ia).

By acidifying the mother liquor and working up in the customary manner it is possible to recover 19.6 g of 4-amino-3-mercapto-6-tert.-butyl-1,2,4-triazin-5-one (II).

It will be understood that the specification and and examples are illustrative but not limitative of the present invention and that other embodiments within the spirit and scope of the invention will suggest themselves to those skilled in the art.

I claim:

1. In the preparation of amino-3-ethylthio-6-tert.-butyl-1,2,4-triazin-5-one (I) by reacting 4-amino-3-mercapto-6-tert.-butyl-1,2,4-triazin-5-one (II) with an ethylating agent in aqueous alkali solution, the improvement which comprises contacting the reaction mixture with at least 50 g of petroleum ether per mole of starting compound (II) at a temperature of about 40°-60° C. thereby forming two liquid phases, and cooling the mixture down to about room temperature, whereby substantially pure isomer-free end product of the formula (I) crystallizes out.

2. A process according to claim 1, wherein the reaction is carried out at a temperature of about 40°-50° C.

3. A process according to claim 1, wherein about 50-400 g of petroleum ether are used per mole of starting compound (II).

4. A process according to claim 3, wherein about 100-250 g of petroleum ether are used per mole of starting compound (II).

5. A process according to claim 1, wherein the petroleum ether has a boiling range from about 100° to 140° C.

* * * * *